United States Patent [19]

Riediker et al.

[11] Patent Number: 4,857,654
[45] Date of Patent: Aug. 15, 1989

[54] TITANOCENES AND THEIR USE

[75] Inventors: Martin Riediker, Riehen; Eginhard Steiner, Füllinsdorf; Harry Beyeler, Basel; Manfred Rembold, Aesch; Franciszek Sitek, Therwil, all of Switzerland

[73] Assignee: Ciba-Geigy Corporation, Ardsley, N.Y.

[21] Appl. No.: 77,261

[22] Filed: Jul. 24, 1987

[30] Foreign Application Priority Data
Aug. 1, 1986 [CH] Switzerland .......................... 3101/86

[51] Int. Cl.$^4$ ............................................. C07F 7/28
[52] U.S. Cl. ...................................... 556/53; 556/11; 430/281; 430/325
[58] Field of Search .............................. 558/53; 556/11

[56] References Cited

U.S. PATENT DOCUMENTS 4,590,287  5/1986  Riediker et al. ...................... 556/53

*Primary Examiner*—Michael L. Shippen
*Attorney, Agent, or Firm*—Luther A. R. Hall

[57] ABSTRACT

Titanocenes with, for example, $\pi$-cyclopentadienyl ligands in which one or two carbo- or heterocyclic aromatic rings are bonded to the titanium, the aromatic rings being substituted by fluorine in at least one of the two ortho-positions relative to the metal-carbon bond and being substituted by at least one free or etherified or esterified polyoxaalkylene radical, are suitable as photoinitiators for the photopolymerization of ethylenically unsaturated substrates.

12 Claims, No Drawings

TITANOCENES AND THEIR USE

The present invention relates to titanocenes with fluorinated aromatic radicals, a photopolymerizable composition of ethylenically unsaturated compounds which contain these titanocenes as photoinitiators, a substrate coated with this composition and a process for the production of photographic relief images using this coated substrate.

It is known from European Patent No. A-0,122,223 that titanocenes with fluoroaryl ligands are excellent photoinitiators. These titanocenes are crystalline and therefore cannot always be processed technologically without problems. The photosensitivities which can be achieved with these titanocenes are influenced by their solubilities in photosensitive compositions.

The present invention relates to titanocenes of the formula I

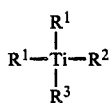
(I)

in which the two radicals $R^1$ independently of one another are cyclopentadienyl$\ominus$, indenyl$\ominus$ or 4,5,6,7-tetrahydroindenyl$\ominus$ unsubstituted or mono- or polysubstituted by $C_1$-$C_{18}$-alkyl or -alkoxy, $C_2$-$C_{18}$-alkenyl, $C_5$-$C_8$-cycloalkyl, $C_6$-$C_{16}$-aryl $C_7$-$C_{16}$-aralkyl, cyano or halogen, or the two radicals $R^1$ together are a radical, unsubstituted or substituted as described above, of the formula II

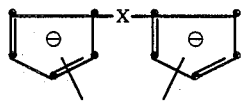
(II)

in which X is (—$CH_2$—)n, where n is 1, 2 or 3, alkylidene which has 2 to 12 C atoms and is unsubstituted or substituted by phenyl, cycloalkylidene which has 5 to 7 ring carbon atoms, $SiR_2^4$ or $SnR_2^4$ and $R^4$ is $C_1$-$C_{12}$-alkyl, $C_5$-$C_{12}$-cycloalkyl, $C_6$-$C_{16}$-aryl or $C_7$-$C_{16}$-aralkyl, $R^2$ is a 6-membered carbocyclic or 5- or 6-membered heterocyclic aromatic ring which is substituted by fluorine atoms in at least one of the two ortho-positions relative to the metal-carbon bond, it being possible for the aromatic ring to contain further substituents, or $R^2$ and $R^3$ together are a radical of the formula III

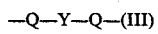(III)

in which Q is a carbocyclic aromatic ring, the two bonds in each case being in the ortho-position relative to the Y group, and the meta-position relative to the Y group in each case being substituted by a fluorine atom, and it being possible for Q to contain further substituents, and Y is $CH_2$, alkyl-idene with 2 to 12 C atoms, cycloalkylidene with 5 to 7 ring carbon atoms, a direct bond, $NR^4$, O, S, SO, $SO_2$, CO, $SiR_2^4$ or $SnR_2^4$ and $R^4$ is as defined above, $R^3$ has the meaning of $R^2$ or is alkynyl, substituted or unsubstituted phenylalkynyl, $N_3$, CN, $SiR_3^4$, in which titanocenes $R^2$ contains at least one (polyoxaalkylene) radical which is free, etherified or esterified, this radical being bonded to the aromatic ring either directly or via a bridge group.

The groups $R^1$ are preferably the same radicals. Possible substituents for $R^1$ are: linear or branched alkyl or alkoxy with 1 to 18, in particular 1 to 12 and especially 1 to 6 C atoms and alkenyl with 2 to 18, in particular 2 to 12 and especially 2 to 6 C atoms, for example methyl, ethyl, propyl, isopropyl, n-butyl, tert.-butyl, pentyl, hexyl, octyl, decyl, dodecyl, tetradecyl, hexadecyl, octadecyl and corresponding alkenyl and alkoxy groups; cycloalkyl and cycloalkenyl with 5 to 8 ring carbon atoms, for example cyclopentyl, cyclohexyl, cycloheptyl, methylpentyl and methylcyclohexyl; aryl with 6 to 16 C atoms and aralkyl with 7 to 16 C atoms, for example phenyl, naphthyl, benzyl and phenethyl; nitrile and halogen, in particular F, Cl and Br.

The radicals $R^1$ can contain up to 3, but in particular 1, substituents. In particular, the two radicals $R^1$ are cyclopentadienyl$\ominus$ or methylcyclopentadienyl$\ominus$ radicals.

Alkylidene X in formula II preferably contains 2 to 6 C atoms. Examples of alkylidene, which can be unsubstituted or substituted by phenyl, and cycloalkylidene are ethylidene, propylidene, butylidene, hexylidene, phenylmethylene, diphenylmethylene, cyclopentylidene and cyclohexylidene. Alkyl $R^4$ in the group X preferably contains 1 to 6 C atoms and is, for example, methyl, ethyl, propyl, butyl or hexyl, and cycloalkyl $R^4$ is preferably cyclopentyl or cyclohexyl, aryl $R^4$ is preferably phenyl and aralkyl $R^4$ is preferably benzyl. X is particularly preferably methylene.

A 6-membered carbocyclic aromatic and fluorine-substituted ring $R^2$ can be fluorine-substituted indene, indane, fluorene, naphthalene and, in particular, phenyl. Preferably, the two ortho-positions are substituted by fluorine. A heterocyclic aromatic 5-membered radical $R^2$ preferably contains one hetero atom, and a 6-membered ring $R^2$ preferably contains 1 or, 2 hetero atoms.

The group $R^2$ contains at least one (polyoxaalkylene) radical which is free, etherified or esterified, it being possible for this radical to be bonded to the aromatic ring directly or via a bridge group. It can contain further ring substituents, for example alkyl, cycloalkyl, aryl, aralkyl, hydroxyl, alkoxy, carboxyl, alkoxycarbonyl, halogen or cyano. Examples of these are: linear or branched alkyl or alkoxy with preferably 1 to 18, in particular 1 to 6, C atoms, for example methyl, ethyl, propyl, butyl, pentyl, hexyl and the corresponding alkoxy groups, in particular methyl and methoxy; cycloalkyl with preferably 5 or 6 ring carbon atoms, aryl with preferably 6 to 16 C atoms and aralkyl with preferably 7 to 16 C atoms, for example cyclopentyl, cyclohexyl, phenyl or benzyl; hydroxyl, carboxyl, CN, halogen, such as F, Cl, or Br, and tertiary amino, which can be quaternized with alkyl halides, such as methyl chloride, bromide or iodide. Examples of amino are dimethylamino, pyrrolidyl, piperidyl, piperazyl, morpholyl and N-methylpiperazyl; alkoxycarbonyl with preferably 1 to 18, in particular 1 to 6, C atoms in the alkoxy group; aminocarbonyl with one or two alkyl groups with 1 to 12 C atoms in the amino group or aminocarbonyl with heterocyclic amines, such as pyrrolidine, piperidine, piperazine, N-methylpiperazine and morpholine; and tertiary aminoalkyl with preferably $C_1$-$C_6$-alkyl groups, which can be quaternized by alkyl halides.

Alkynyl $R^3$ preferably contains 2 to 6 C atoms. Examples are ethynyl and propargyl. Phenylalkynyl $R^3$ is preferably phenylethynyl. Substituents for phenylalkynyl $R^3$ are, for example, halogen, such as F, Cl or Br, tertiary amino and alkoxy with 1 to 6 C atoms, carboxyl, OH and CN. $R^3$ preferably has the meaning of $R^2$.

In a preferred embodiment, $R^2$ in formula I is substituted 2,6-difluorophen-1-yl, or $R^2$ and $R^3$ together are a substituted radical of the formula

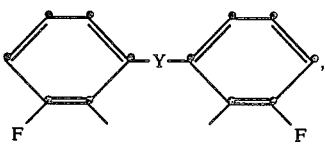

in which Y has the abovementioned meaning, and are substituted by at least one free, etherified or esterified (polyoxa-alkylene) radical, it being possible for this radical to be bonded to $R^2$ directly or via a bridge group. In particular, $R^2$ is 2,6-difluorophen-1-yl which contains 1 to 3 further substituents, at least one of which is a free, etherified or esterified (polyoxaalkylene) radical which is bonded to $R^2$ directly or via a bridge group.

In a preferred embodiment, $R^2$ and $R^3$ are 2,6-difluorophen-1-yl, to which at least one free or etherified polyoxaalkylene radical is bonded directly or via a bridge group and which can contain 1 or 2 further identical or different substituents.

A preferred group of metallocenes of the formula I are those in which the two radicals $R^1$ are cyclopentadienyl-or cyclopentadienyl$\ominus$ which is substituted by $C_1$–$C_4$-alkyl, and $R^2$ and $R^3$ are radicals of the formula

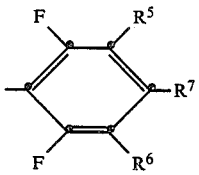

in which $R^5$ and $R^6$ independently of one another are H, F, Cl or Br and $R^7$ is polyoxaalkylene which is free, etherified or esterified and is bonded to the phenyl ring directly or via a bridge group. $R^5$ and $R^6$ are preferably F.

The polyoxaalkylene radical is preferably etherified with $C_1$–$C_{18}$-, in particular $C_1$–$C_{12}$- and especially $C_1$–$C_6$ alkyl or esterified with $C_1$–$C_{18}$-, in particular $C_1$–$C_{12}$- and especially $C_1$–$C_6$-acyl. Examples of alkyl are methyl, ethyl, n- and i-propyl, n-, i- and t-butyl, pentyl, hexyl, heptyl, octyl, nonyl, decyl, undecyl, dodecyl, tetradecyl, hexadecyl and octadecyl. Examples of acyl are formyl, acetyl, propionyl, trifluoroacetyl, butyryl, pentanoyl, hexanoyl, octanoyl, dodecanoyl and benzoyl. Etherified poly-oxaalkylene radicals are preferred.

The polyoxaalkylene radical preferably contains 1 to 20, in particular 1 to 12 and especially 2 to 6 oxaalkylene units. The alkylene in the (polyoxaalkylene) radical preferably contains 2 to 6, in particular 2 to 4, C atoms and is, in particular, ethylene or 1,2-propylene. Other examples are 1,3-propylene, 1,2-, 1,3- and 1,4-butylene, pentylene and hexylene. The polyoxaalkylene radical can also contain various alkylene radicals.

In a preferred embodiment, the polyoxaalkylene radical corresponds to the formula $-(C_zH_{2z}O)_oR^9$, in which z is a number from 2 to 6, o is a number from 1 to 20 and $R^9$ is H or $C_1$–$C_{18}$-alkyl.

In a preferred group of titanocenes according to the invention, the bridge group is a group of the formula —S—, —O—, —OSO$_2$—, —CH$_2$—, —CH(CH$_3$)O—, —SO$_2$—, —C(O)O—,

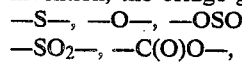

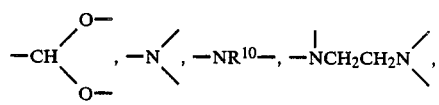

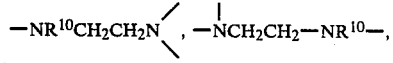

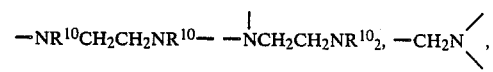

—CH$_2$NR$^{10}$—, —CH(COO—)$_2$, —CH$_2$COO—, —CONR$^{10}$—, —CH(CONR$^{10}$—)$_2$,

—OC(O)O—, —N(R$^{10}$)—COO—, —CH$_2$N(R$^1$-$^0$)—COO—, —N(R$^{10}$)—CONH—, —CH$_2$N(R$^1$-$^0$)—CONH—or —C$_n$N$_{2n}$OC(O)C$_m$H$_{2m}$O—where n=0, 1 or 2 and m=1–6, —C$_n$H$_{2n}$OSiR$_{3-y}^{11}$O$_y$—, where n=0, 1 or 2 and y=1–3, or —OCH$_2$CH$_2$OSiR$_{3-y}^1$-$^1$O$_y$—, where y=1–3, in which $R^{10}$ is H, $C_1$–$C_{18}$-alkyl or $C_1$–$C_{18}$-acyl and $R^{11}$ is $C_1$–$C_{12}$-alkyl or phenyl.

In a preferred embodiment, $R^9$ is $C_1$–$C_{12}$-alkyl, $R^{10}$ is H or $C_1$–$C_{12}$-alkyl and $R^{11}$ is $C_1$–$C_6$-alkyl, z is a number from 2 to 4 and o is a number from 2 to 6.

In a particularly preferred group of the titanocenes according to the invention, the polyoxaalkylene radical bonded via a bridge group corresponds to the formulae $-O(CH_2CH_2O)_oR^9$

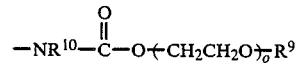

$-N[(CH_2CH_2-O)_oR^9]_2$ $-NR^{10}(CH_2CH_2O)_oR^9$

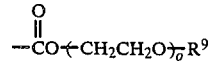

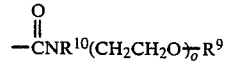

or

-continued

in which $R^9$ is $C_1$–$C_{12}$-alkyl, $R^{10}$ is H or $C_1$–$C_6$-alkyl and o is a number from 2 to 6.

Particularly preferred titanocenes of the formula I are those in which $R^1$ is cyclopentadienyl or methylcyclopentadienyl and $R^2$ and $R^3$ are radicals of the formula

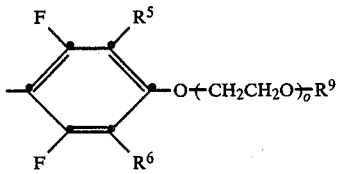

in which $R^5$ and $R^6$ are hydrogen or fluorine, o is a number from 2 to 6 and $R^9$ is $C_1$–$C_{12}$-alkyl, in particular those in which $R^5$ and $R^6$ are fluorine.

Examples of titanocenes of the formula I are: bis(cyclopentadienyl)-bis[4-(1′,4′,7′-trioxaundecyl)-2,3,5,6-tetrafluorophenyl]-titanium, bis(methylcyclopentadienyl)-bis-[4-(1′,4′,7′-trioxaundecyl)-2,3,5,6-tetrafluorophenyl]-titanium, bis(cyclopentadienyl)-bis[4-(1′,4′,7′,10′-tetraoxado-decyl)-2,3,5,6-tetrafluorophenyl]-titanium, bis(methylcyclopentadienyl)-bis[3-(1′,4′,7′-trioxahendecyl)-2,6-difluoro-phenyl]-titanium, bis(cyclopentadienyl)-bis[3-(1′,4′,7′,10′-trioxadodecyl)-2,6-difluorophenyl]-titanium and bis(cyclo-pentadienyl)-bis[3-(1′,4′-dioxapentyl)-2,6-difluorophenyl]-titanium.

The titanocenes of the formula I can be prepared by known processes or analogous processes, by reacting 1 mol of a compound of the formula III

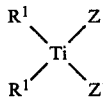 (III)

in which $R^1$ is as defined and Z is halogen, in particular chlorine, either with one mol of LiR$^2$ or LiR$^3$ and then with one mol of LiR$^3$ and LiR$^2$ respectively, or with 2 mol of LiR$^2$, in which $R^2$ is as defined above and $R^3$ is alkynyl, unsubstituted or substituted phenylalkynyl, N$_3$, CN, SiR$_3^4$ or SnR$_3^4$, and then isolating the compounds of the formula I in a manner which is known per se.

The known processes are described, for example, in J. Organometal. Chem., 2 (1964) 206–212, J. Organometal. Chem., 4 (1965) 445–446 and in European Patent A-0,122,223.

The starting compounds of the formula III in which Z represents, in particular, chlorine are known or can be obtained by analogous processes by reacting TiCl$_4$ with sodium compounds NaR$^1$. The lithium compounds LiR$^2$ and LiR$^3$ are likewise known or can be prepared by analogous processes by reacting R$^2$- or R$^3$-halides, in particular the bromides, with butyllithium. Derivatives substituted by tertiary aminomethyl groups are obtained, for example, by reacting corresponding difluorodibromophenyl compounds, which are first converted into lithium difluorobromophenyl compounds and then reacted with N,N-dialkylmethyleneammonium chloride, after which the dialkylaminomethyldifluorobromophenyl formed is reacted with butyllithium to give the corresponding lithium compound.

The free, etherified or esterified polyoxaalkylene radical is introduced into the R$^2$-halides in a manner which is known per se. Functional R$^2$-halides which contain suitable precursors for bridge groups are described, for example, by L. S. Kobrina in Fluorine Chemistry Reviews, Volume 7, pages 1–114, Marcel Dekker Inc., NY, 1974.

The metallocenes of the formula I are in general prepared in the presence of inert solvents, for example hydrocarbons or ethers, at temperatures from below −30° to −100° C., preferably −60° to −90° C., under an inert gas atmosphere. In one embodiment of the process, LiR$^2$ or LiR$^3$ is first prepared by reacting the corresponding halides with lithium butyl in ether as the solvent at temperatures of about −78° C. The corresponding titanocene dihalide is then added to the cooled reaction mixture, the cooling is removed and the mixture is allowed to warm to room temperature. The reaction mixture is then filtered, if necessary after addition of solvents, and the titanocene according to the invention is isolated from the solution by precipitation or by evaporation of the solvent.

They are in general liquid, syrupy to resinous, usually orange-coloured compounds which have a high heat stability and decompose only at high temperatures. No decomposition is observed under the action of air or under the action of water. The compounds can readily be dissolved in curable compositions or mixed with these, even in relatively large amounts, and therefore offer useful practical advantages. The compounds are also very readily soluble in solvents and can be incorporated in the form of solutions into curable compositions, after which the solvent is removed if necessary.

The compounds are stable to storage in the dark and can be handled without an inert gas. By themselves, they are outstandingly suitable as highly effective photoinitiators for light-induced polymerization of ethylenically unsaturated compounds. They are distinguished here by a very high photosensitivity and effectiveness over a wide wavelength range from about 200 nm (UV light) to about 600 nm. The titanocenes are furthermore also capable of effectively initiating polymerization under the influence of heat, heating to 170° C. to 240° C. being advantageous. The action of light and heating can of course be utilized for the polymerization, heating after exposure to light allowing lower temperatures, for example 80°–150° C., for the polymerization.

The present invention furthermore relates to a composition which can be polymerized by radiation and contains (a) at least one non-volatile monomeric, oligomeric or polymeric compound with at least one polymerizable ethylenically unsaturated double bond and (b) at least one titanocene of the formula I as a photoinitiator.

The compositions can contain further photoinitiators (c), for example those of the benzil ketal, 4-aroyl-1,3-dioxolane, dialkoxyacetophenone or α-hydroxy- or α-amino-acetophenone type or mixtures thereof. The advantage is that smaller amounts of the titanocenes according to the invention can be used and the same or improved photosensitivities can nevertheless be achieved. The weight ratio of these components (c):(b) can be, for example, from 1:1 to 30:1, preferably 5:1 to 15:1.

The amount of titanocenes according to the invention added essentially depends on economic viewpoints, their solubilities and the desired sensitivity. In general, 0.01 to 20, preferably 0.05–10 and especially 0.1 to 5% by weight is used, based on component (a).

Possible components (a) are those ethylenically unsaturated monomeric, oligomeric and polymeric compounds which react by photopolymerization to give higher molecular weight products and change their solubility in doing so.

Compounds which are particularly suitable are, for example, esters of ethylenically unsaturated carboxylic acids and polyols or polyepoxides, and polymers with ethylenically unsaturated groups in the chain or in side groups, for example unsaturated polyesters, polyamides and polyurethanes and copolymers thereof, polybutadiene and butadiene copolymers, polyisoprene and isoprene copolymers, polymers and copolymers with (meth)acrylic groups in side chains, and mixtures of one or more such polymers.

Examples of unsaturated carboxylic acids are acrylic acid, methacrylic acid, crotonic acid, itaconic acid, cinnamic acid and unsaturated fatty acids, such as linolenic acid or oleic acid. Acrylic and methacrylic acid are preferred.

Suitable polyols are aromatic and, in particular, aliphatic and cycloaliphatic polyols. Examples of aromatic polyols are hydroquinone, 4,4′-dihydroxydiphenyl, 2,2-di(4-hydroxyphenyl)-propane, novolaks and resols. Examples of polyepoxides are those based on the polyols mentioned, in particular the aromatic polyols and epichlorohydrin. Polymers or copolymers which contain hydroxyl groups in the polymer chain or in side groups, for example polyvinyl alcohol and copolymers thereof, or polymethacrylic acid hydroxyalkyl esters or copolymers thereof, are furthermore also suitable as polyols. Other suitable polyols are oligoesters with hydroxyl end groups.

Examples of aliphatic and cycloaliphatic polyols are alkylenediols with preferably 2 to 12 C atoms, such as ethylene glycol, 1,2- or 1,3-propanediol, 1,2-, 1,3- or 1,4-butanediol, pentanediol, hexanediol, octanediol, dodecane-diol, diethylene glycol, triethylene glycol, polyethylene glycols with molecular weights of preferably 200 to 1,500, 1,3-cyclopentanediol, 1,2-, 1,3- or 1,4-cyclohexanediol, 1,4-dihydroxymethylcyclohexane, glycerol, tris-(β-hydroxyethyl)-amine, trimethylolethane, trimethylolpropane, pentaerythritol, dipentaerythritol and sorbitol.

The polyols can be partly or completely esterified with one or several unsaturated carboxylic acids, it being possible for the free hydroxyl groups in part esters to be modified, for example etherified, or esterified with other carboxylic acids.

Examples of esters are: trimethylolpropane triacrylate, trimethylolethane triacrylate, trimethylolpropane trimethacrylate, trimethylolethane trimethacrylate, tetramethylene glycol dimethacrylate, triethylene glycol dimethacrylate, tetraethylene glycol diacrylate, pentaerythritol diacrylate, pentaerythritol triacrylate, pentaerythritol tetraacrylate, dipentaerythritol diacrylate, dipentaerythritol triacrylate, dipentaerythritol tetraacrylate, dipentaerythritol pentaacrylate, dipentaerythritol hexaacrylate, tripentaerythritol octaacrylate, pentaerythritol dimethacrylate, pentaerythritol trimethacrylate, dipentaerythritol dimethacrylate, dipentaerythritol tetramethacrylate, tripentaerythritol octamethacrylate, pentaerythritol diitaconate, dipentaerythritol trisitaconate, dipentaerythritol pentaitaconate, dipentaerythritol hexaitaconate, ethylene glycol dimethacrylate, 1,3-butanediol diacrylate, 1,3-butanediol dimethacrylate, 1,4-butanediol diitaconate, sorbitol triacrylate, sorbitol tetraacrylate, sorbitol tetramethacrylate, sorbitol pentaacrylate, sorbitol hexaacrylate, oligoester acrylates and methacrylates, glycerol di- and triacrylate, 1,4-cyclohexane diacrylate, bisacrylates and bismethacrylates of polyethylene glycol with a molecular weight of 200–1,500, or mixtures thereof.

Suitable components (a) are also the amides of identical or different unsaturated carboxylic acids of aromatic cycloaliphatic and aliphatic polyamines with preferably 2 to 6, in particular 2 to 4, amino groups. Examples of such polyamines are ethylenediamine, 1,2- or 1,3-propylenediamine, 1,2-, 1,3- or 1,4-butylenediamine, 1,5-pentylenediamine, 1,6-hexylenediamine, octylenediamine, dodecylenediamine, 1,4-di-aminocyclohexane, isophorondiamine, phenylenediamine, bisphenylenediamine, di-β-aminoethyl ether, diethylenetriamine, triethylenetetramine and di-(8-aminoethoxy)- or di(β-amino-propoxy)-ethane. Other suitable polyamines are polymers and copolymers with amino groups in the side chain and oligo-amides with amino end groups.

Examples of such unsaturated amides are: methylene-bis-acrylamide, 1,6-hexamethylene-bis-acrylamide, diethylene-triamine-tris-methacrylamide, bis(methacrylamidopropoxy)-ethane, β-methacrylamidoethyl methacrylate and N[(8-hydroxy-ethoxy)ethyl]-acrylamide.

Suitable unsaturated polyesters and polyamides are derived, for example, from maleic acid and diols or diamines. The maleic acid can in part be replaced by other dicarboxylic acids. These can be used together with ethylenically unsaturated comonomers, for example styrene. The polyesters and polyamides can also be derived from dicarboxylic acids and ethylenically unsaturated diols or diamines, in particular from longer-chain compounds with, for example, 6 to 20 C atoms. Examples of polyurethanes are those which are built up from saturated or unsaturated diisocyanates and unsaturated or saturated diols.

Polybutadiene and polyisoprene and copolymers thereof are known. Examples of suitable comonomers are polyolefins, such as ethylene, propene, butene, hexene, (meth)acrylates, acrylonitrile, styrene or vinyl chloride.

Polymers with (meth)acrylate groups in the side chain are likewise known. These can be, for example, reaction products of novolak-based epoxy resins with (meth)acrylic acid, homo- or copolymers of polyvinyl alcohol or hydroxyalkyl derivatives thereof esterified with (meth)acrylic acid, or homo- and copolymers of (meth)acrylates esterified with hydroxyalkyl (meth)acrylates.

The photopolymerizable compounds can be used by themselves or in any desired mixtures. Mixtures of polyol (meth)acrylates are preferred.

Binders can also be added to the compositions according to the invention, which is particularly advantageous if the photopolymerizable compounds are liquid or viscous substances. The amount of binder can be, for example, 5–95, preferably 10–90 and in particular 50–90% by weight, based on the total composition. The binder is chosen according to the field of use and the properties required for this, such as ease of development in aqueous and organic solvent systems, adhesion to substrates and sensitivity to oxygen.

Examples of suitable binders are polymers with a molecular weight of about 5,000–2,000,000, preferably 10,000 to 1,000,000. Examples are: homo- and copolymeric acrylates and methacrylates, for example copolymers of methyl methacrylate/ethyl acrylate/methacrylic acid, poly(methacrylic acid alkyl esters) and poly(acrylic acid alkyl esters); cellulose esters and ethers, such as cellulose acetate, cellulose acetobutyrate, methylcellulose and ethylcellulose; polyvinylbutyral, polyvinylformal, cyclized rubber and polyethers such as polyethylene oxide, polypropylene oxide and polytetrahydrofuran; polystyrene, polycarbonate, polyurethane, chlorinated polyolefins, polyvinyl chloride, copolymers of vinyl chloride/vinylidene chloride, copolymers of vinylidene chloride with acrylonitrile, methyl methacrylate and vinyl acetate, polyvinyl acetate, copoly(ethylene/vinyl acetate), polyamides such as polycaprolactam and poly(hexamethyleneadipamide), and polyesters such as poly(ethylene glycol terephthalate) and poly(hexamethylene glycol succinate).

The compositions according to the invention are suitable as coating agents for all types of substrate, for example wood, paper, ceramics, plastics, such as polyester and cellulose acetate films, and metals, such as copper and aluminium, in which a protective layer or a photographic image is to be applied by photopolymerization. The present invention furthermore relates to the coated substrates and a process for the application of photographic images to the substrates.

The substrates can be coated by applying a liquid composition, a solution or suspension to the substrate. Liquid compositions without a solvent are preferred. It may be advantageous here to use the titanocenes according to the invention in the form of a liquid photoinitiator mixture containing other photoinitiators, for example a benzil ketal, a 4-aroyl-1,3-dioxolane, a dialkoxyacetophenone, an α-hydroxy- or α-aminoacetophenone, or mixtures thereof. Liquid mixtures of liquid to solid photoinitiators and liquid titanocenes or liquid photoinitiators and syrupy to solid titanocenes are particularly advantageous. These mixtures offer practical advantages and are distinguished by a high stability when stored in the dark.

Examples of benzil ketals are those of the formula

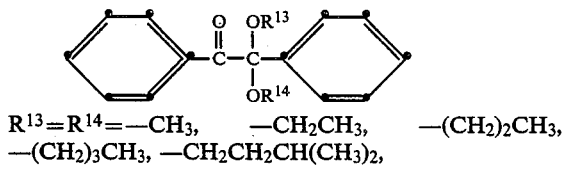

$R^{13}=R^{14}=-CH_3$, $-CH_2CH_3$, $-(CH_2)_2CH_3$, $-(CH_2)_3CH_3$, $-CH_2CH_2CH(CH_3)_2$,

$-(CH_2)_9CH_3$, $-C_{10}H_{21}$-iso, $-C_{12}H_{25}$-n, $-C_9H_{19}$ to $-C_{11}H_{23}$ mixture, $-C_{12}$-$H_{25}$ to $-C_{15}H_{31}$ mixture, $-CH_2CH=CH_2$, $-CH(CH_3)CH=CH_2$, $-CH_2C-H_2OC_3H_7$-iso, $-CH_2CH_2OC_4H_9$, $-CH_2OCH_2OCH_2CH=CH_2$, $-CH(CH_3)-CH_2OC_4H_9$, $-CH_2COOCH_3$, $-CH_2COOC_4H_9$, $-CH(CH_3)COOCH_3$, $-CH_2CH_2COOC_2H_5$, $-CH(CH_3)CH_2COOCH_3$, $-CH_2, CH_2CH(CH_3)OCH_3$,

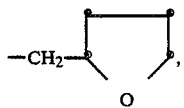

$-(CH_2CH_2O)_2CH_3$, $-(CH_2CH_2O)_2C_2H_5$, $-(CH_2CH_2O)_2C_4H_9$, $-(CH_2CH_2O)_3CH_3$, $-(CH_2C-H_2O)_3C_2H_5$, $-(CH_2CH_2O)_3C_{12}H_{25}$, $-(CH_2C-H_2O)_5C_{10}H_{21}$—$(CH_2CH_2O)_8C_9H_{19}$ to $-C_{11}H_{23}$ (mixture),

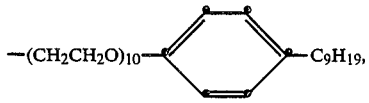

$-CH_2CH_2N(C_2H_5)_2$,

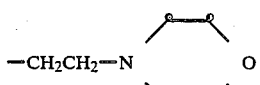

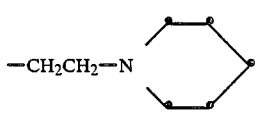

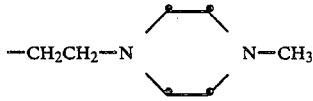

$R^{14}=CH_3$ and $R^{13}=C_6H_{13}$, $R^{14}=CH_3$ and $R^{13}=C_{10}H_{21}$, $R^{14}=CH_3$ and $R^{13}=(-CH_2CH_2O)_3C_{12}H_{25}$ to $-C_{15}H_{31}$ (mixture), $R^{14}=CH_3$ and $R^{13}=(-CH_2C-H_2O)_5C_9H_{19}$ to $-C_{11}H_{23}$ (mixture) or $R^{14}=CH_3$ and $R^{13}{}_{13}=CH_3$ and $R^{13}=$,

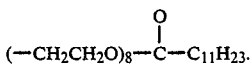

Examples of 4-aroyl-1,3-dioxolanes are: 2,2,4-trimethyl-1,3-dioxolane, 4-benzoyl-4-methyl-2,2-tetra-methylene-1,3-dioxolane, 4-benzoyl-4-methyl-2,2-pentamethyl-ene-1,3-dioxolane, cis-trans-4-benzoyl-2,4-dimethyl-2-methoxy-methyl-1,3-dioxolane, cis-trans-4-benzoyl-4-methyl-2-phenyl-1,3-dioxolane, 4-(4-methoxybenzoyl)-2,2,4-trimethyl-1,3-dioxolane, 4-(4-methoxybenzoyl)-4-methyl-2,2-pentamethylene-1,3-dioxolane, 4-(4-methylbenzoyl)-2,2,4-trimethyl-1,3-dioxo-lane, cis-trans-4-benzoyl-2-methyl-4-phenyl-1,3-dioxolane,4-benzoyl-2,2,4,5,5-pentamethyl-1,3-dioxolane, cis-trans-4-benzoyl-2,2,4,5-tetramethyl-1,3-dioxolane, cis-trans-4-benzoyl-4-methyl-2-pentyl-1,3-dioxolane, cis-trans-4-benzoyl- 2-benzyl-2,4-dimethyl-1,3-dioxolane, cis-trans-4-benzoyl-2-(2-furyl)-4-methyl-1,3-dioxolane, cis-trans-4-benzoyl-5-phenyl-2,2,4-trimethyl-1,3-dioxolane and 4-(4-methoxy-benzoyl)-2,2,4,5,5-pentamethyl-1,3-dioxolane.

Examples of dialkoxyacetophenones are: α,α-dimethoxyacetophenone, α,α-diethoxyacetophenone, α,α-di-iso-propoxyacetophenone, α,α-di-(2-methoxyethoxy)acetophenone, α-butoxy-α-ethoxyacetophenone, α,α-dibtoxy-4-chloroaceto-phenone, m,α-diethoxy-4- fluoroacetophenone, α,α-dimethoxy-4-methylacetophenone, α,α-dimethoxy-4-methylacetophenone, α,α-dimethoxypropiophenone, α,α-diethoxypropiophenone, α,α-di-ethoxybutyrophenone, α,α-dimethoxyisovalerophenone, α,α-di-ethoxy-α-cyclohexylacetophenone and q,α-dipropoxy-4-chloro-propiophenone.

Examples of α-hydroxy- and u-aminoacetophenones are: 2-hydroxy-2-methyl-1-phenyl-propan-1-one, 2-hydroxy-2-ethyl-1-phenylhexan-1-one, 1-(4-dodecylphenyl)-2-ydroxy-2-methyl-propan-1-one, 1-(2,4-dimethylphenyl)-2-hydroxy-2-methyl-propan-1-one, 2-hydroxy-1-(4-methoxyphenyl)-2-methylpropan-1-one, 2-hydroxy-2-methyl-1-phenylbutan-1-one, 2-dimethylamino-2-methyl-1-phenylpropan-1-one, 2-dibutylamino-2-methyl-1-phenylpropan-1-one, 1-(4-fluorophenyl)-2-methyl-2-morpho-linopentan-1-one, 2-methyl-1-(4-methylthiophenyl)-2-morpholinobutan-1-one, 2-dimethylamino-1-(4-methoxyphenyl)-2-methylpropan-1-one and 2-diethylamino-1-(4-diethylamino-phenyl)-2-methylpropan-1-one.

The photoinitiator mixture (b)+(c) can be added in amounts of 0.5–20, preferably 1 to 10, % by weight, based on component (a).

The choice of solvent and the concentration depends chiefly on the nature of the composition and on the coating process. The composition is applied uniformly to a substrate by means of known coating processes, for example by dipping, knife coating, the curtain coating process, electrophoresis, brushing on, spraying or reverse roll coating. The amount applied (coating thickness) and nature of the substrate (layer carrier) depend on the desired field of application. Films of polyester, cellulose acetate or paper coated with plastic, for example, are used as layer carriers for photographic recording of information; specially treated aluminium is used for offset printing plates and copper-lined laminates are used for production of printed circuits. The layer thicknesses for photographic materials and offset printing plates are in general about 0.5 to about 10 μm; for printed circuits they are in general 1 to about 100 μm. If solvents are also used, these are removed after the coating operation.

Photocurable compositions such as are used for the various purposes usually contain a number of other additives in addition to the photopolymerizable compounds and the photoinitiators. It is thus frequently customary to add thermal inhibitors which are intended to provide protection from premature polymerization, above all during preparation of the compositions by mixing of the components. Inhibitors which are used for this are, for example, hydroquinone, hydroquinone derivatives, p-methoxyphenol, β-naphthols or sterically hindered phenols, for example 2,6-di(tert.-butyl)-p-cresol. Small amounts of UV absorbers can furthermore be added, for example those of the benzotriazole, benzophenone or oxalanilide type. Light stabilizers of the sterically hindered amine type (HALS) can also be added.

Copper compounds, such as copper naphthenate, stearate or octoate, phosphorus compounds, such as triphenylphosphine, tributylphosphine, triethyl phosphite, triphenyl phosphite or tribenzyl phosphite, quaternary ammonium compounds, such as tetramethylammonium chloride or triethyl-benzylammonium chloride, or hydroxylamine derivatives, for example N-diethylhydroxylamine, can be added to increase the stability to storage in the dark.

Paraffin or similar waxy substances are frequently added to photocurable mixtures in order to exclude the inhibiting effect of atmospheric oxygen. When polymerization starts, these float out due to a lack of solubility in the polymer and form a transparent surface layer which prevents Other customary additives are photosensitizers which absorb in certain wavelengths and release the absorbed energy to the initiators or themselves function as an additional initiator. Examples of these are, above all, thioxanthone, anthracene, anthraquinone and coumarin derivatives.

Other customary additives are accelerators of the amine type, which are of importance above all in pigmented formulations since they act as chain transfer agents. Examples of these are N-methyldiethanolamine, triethylamine, ethyl p-dimethylaminobenzoate or Michler's ketone. The action of the amines can be intensified by addition of aromatic ketones of the benzophenone type.

Examples of other customary additives are fillers, pigments, dyes, adhesives, wetting agents and flow control agents.

Photocuring is of great importance for printing inks, since the drying time of the binder is a decisive factor for the rate of production of graphics products and should be of the order of fractions of seconds. UV-curable printing inks are of particular importance for screen printing.

The photocurable compositions according to the invention are also particularly suitable for the production of printing plates, in particular flexographic printing plates, mixtures of soluble linear polyamides or styrene-butadiene rubber with photopolymerizable monomers, for example acrylamides or acrylates, and a photoinitiator are used, for example, for this. Films and plates of these systems are exposed via the negative (or positive) of the print master and the non-cured portions are then eluted with a solvent.

Another field of use of photocuring is coating of metals, for example varnishing of sheet metal for tubes, cans or bottle caps, and photocuring of coatings of plastic, for example PVC-based floor or wall coverings.

Examples of photocuring of coatings on paper are colourless varnishing of labels, record sleeves or book jackets.

The use of the photocurable compositions for imaging processes and for optical production of information carriers is also of importance. Here, the layer (wet or dry) applied to the carrier is irradiated with short wavelength light through a photomask and the non-exposed areas of the coating are removed by treatment with a solvent (=developer). The exposed areas are cross-linked-polymeric and are hence insoluble, and remain on the carrier. When coloured appropriately, visible images result. If the carrier is a metallized layer, after exposure and development the metal can be etched away or thickened by electroplating on the non-exposed areas. Printed circuits and photoresists can be produced in this manner.

Light sources which are suitable for the exposure are those with a high content of short wavelength light. Appropriate technical devices and various types of lamp are available for this. Examples are carbon arc lamps, xenon arc lamps, mercury vapour lamps, metal-halogen lamps, fluorescent lamps, argon lamps or photographic floodlight lamps. Laser light sources have also recently been used. These have the advantage that no photomasks are necessary; the controlled laser beam writes directly onto the photocurable layer.

The titanocenes according to the invention can readily be mixed with the components of the photocurable compositions or are readily soluble in the composition, which means that a high photosensitivity can be achieved.

The examples which follow illustrate the invention in more detail.

EXAMPLE 1

(a) Diethylene glycol mono-butyl mono-(2,3,5,6-tetrafluoro-4-chloro)-phenyl ether 23 g of finely cut Na metal (1 mol) are introduced into 500 ml of diethylene glycol monobutyl ether, the temperature of the mixture being kept at about 45oC by external cooling. When the reaction has subsided, the mixture is warmed to 50oC, until the sodium has dissolved completely. The brown solution is allowed to run into 233 g of chloro-pentafluorobenzene (1.16 mol) at 40°-45° C. in the course of 1 hour, with gentle cooling. The reaction mixture is heated at 70° C. and is kept at this temperature for about 7 hours. After cooling, it is poured onto 1 l of water and extracted with 1 l of methylene chloride. The organic phase is separated off and dried with Na2S04, and the solvent is distilled off under a waterpump vacuum. The residue is rectified under a high vacuum, and the fraction which boils at 100–104° C. under 3 mbar is collected. 280 g of a clear colourless oil is obtained. b) Bis(cyclopentadienyl)-bis-[4-(1',4',7'-trioxa-n-undec-1-yl-(2,3,5,6-tetrafluorophenyl)]titanocene 51.7 g of diethylene glycol mono-butyl mono(2,3,5,6-tetrafluoro-4-chloro)-phenyl ether (0.15 mol) are dissolved in 400 ml of absolute diethyl ether under an argon inert gas atmosphere and the solution is cooled to −75° C. After drop-wise addition of 103 ml of lithium-butyl-hexane solution (1.6 molar), the mixture is stirred at −75° C. for 15 minutes. Thereafter, 18.7 g of biscyclopentadienyl titanium dichloride (0.075 mol) are added in the form of a powder and the cooling is removed. The mixture heats up to room temperature in the course of about 2 hours, an orange-red cloudy solution being formed. The reaction mixture is poured onto 1 l of water and extracted with a total of 600 ml of ethyl acetate in portions. The organic phase is dried with Na2O4 and evaporated under a waterpump vacuum. The residue consists of 58.0 g of a clear orange-red oil. This oil can be purified by chromatography over silica gel with a 2:1 hexane-ether mixture as the mobile phase. The clear viscous orange oil which results after the solvent has been distilled off also remains liquid even after standing for a prolonged period of time.

EXAMPLE 2

An analogous product with similar properties can be prepared if an equivalent amount of bis(methylcyclopentadienyl)titanium dichloride is used as the titanium compound and the procedure followed is otherwise according to the above process. Bis(methylcyclopentadieyl)-bis-[4-(1',4',7'-trioxa-n-undec-1-yl)(2,3,5,6-tetrafluorophenyl)]-titanocene is obtained as a clear viscous orange oil which remains liquid even after standing for a relatively long time.

EXAMPLE 3

Bis(cyclopentadienyl)-bis[4-(1',4',7',10.-tetraoxadodecyl)-2,3,5,6-tetrafluorophenyl]-titanium Triethylene glycol monoethyl ether is reacted with sodium and chloropentafluorobenzene as described in Example 1. The resulting triethylene glycol monoethyl mono(2,3,5,6-tetrafluoro-4-chlorophenyl) ether has a boiling point of 124-128° C. under 8 mbar. 54.1 g of this ether are reacted with 103 ml of lithiumbutyl-hexane solution and 18.7 g of bis-(cyclopentadienyl)titanium dichloride as described in Example 1. After purification by chromatography, the title compound is obtained as a clear viscous orange-coloured oil, which remains liquid even after standing for a relatively long time.

EXAMPLE 4

Photocuring of an acrylate mixture

A photocurable composition is prepared by mixing the following components: 50 parts of an oligourethane-acrylate (Actilan ® AJ 20), 20 parts of trimethylolpropane triacryl-ate, 15 parts of tripropylene glycol diacrylate, 15 parts of N-vinylpyrrolidone and 0.5 part of a silicone-based flow control agent (BYK ® 300, Byk-Mallinckrodt, FRG).

Portions of this composition are mixed with the amount of photoinitiator or initiator mixture stated in the table below. The initiator mixtures are solutions of a titanocene in a liquid initiator of the ketal type of the formula A:

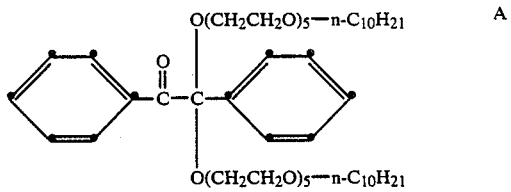

All the operations are carried out under red light or yellow light.

The samples to which initiator has been added are applied in a thickness of 100 μm to aluminium sheets (10×15 cm). A 76 μm thick polyester film is placed on the liquid layer and a standardized test negative with 21 steps of different optical density (Stouffer wedge) is placed on top of this. A second polyester film is placed on top, and the laminate thus obtained is fixed on a metal plate. The sample is then exposed with a 5 KW metal halide lamp at a distance of 30 cm, for 5 seconds in a first test series, 10 seconds in a second test series and 15 seconds in a third test series. After the exposure, the films and mask are removed, the exposed layer is developed in an ethanol bath for 15 seconds and the specimen is then dried at 60° C. for 5 minutes. The sensitivity of the initiator system used is characterized by stating the last wedge step which has been imaged without tackiness. The higher the number of the steps, the more sensitive the system. An increase by two steps here means approximately a doubling of the rate of curing. The results are shown in Table 1.

TABLE 1

| Titanocene initiator | Ketal initiator | Number of steps imaged after | | |
|---|---|---|---|---|
| | | exposure 5 seconds | 10 seconds | 15 seconds |
| 0.2% of Exam- | — | 11 | 12 | 15 |

TABLE 1-continued

| Titanocene initiator | Ketal initiator | Number of steps imaged after exposure | | |
|---|---|---|---|---|
| | | 5 seconds | 10 seconds | 15 seconds |
| ple 1 | | | | |
| 0.2% of Example 1 | 1.8% of A | 11 | 14 | 16 |
| 0.2% of Example 2 | — | 9 | 11 | 13 |

EXAMPLE 5

A photocurable composition is prepared by mixing the following components: 150.3 parts of styrene/-monomethyl maleate copolymer as a 30% solution in acetone, 48.3 parts of trimethylolpropane triacrylate, 6.4 parts of polyethylene glycol diacrylate and 0.16 part of crystal violet.

The procedure followed is as in Example 4. Development is carried out with an aqueous-alkaline solution of the following composition: 1,000 g of water, 15 g of sodium metasilicate, 0.16 g of potassium hydroxide, 3 g of polyethylene glycol 6000 and 0.5 g of levulinic acid.

The results are shown in Table 2.

TABLE 2

| Titanocene initiator | Number of steps imaged after exposure | | |
|---|---|---|---|
| | 20 seconds | 40 seconds | 60 seconds |
| 0.2% of Example 1 | 11 | 14 | 15 |
| 0.2% of Example 2 | 10 | 12 | 14 |

What is claimed is:

1. A titanocene of the formula I

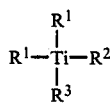

in which the two radicals R1 independently of one another are cyclpentadienyl⊖, indenyl⊖, or 4,5,6,7-tetrahydroindenyl⊖ or said cyclopentadienyl, said indenyl or said 4,5,6,7-tetrahydroindenyl mono- or polysubstituted by $C_1$—$C_{18}$-alkyl, by $C_1$—$C_{18}$-alkoxy, by $C_2$—$C_{18}$-alkenyl, by $C_5$—$C_8$-cycloalkyl, by $C_6$—$C_{16}$-aryl, by $C_7$—$C_{16}$-arakyl, by cyano or by halogen, or the two radicals $R^1$ together are a radical of formula II

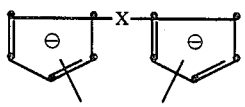

in which X is (—$CH_2$—) n where n is 1, 2 or 3, alkylidene of 2 to 12 carbon atoms, or said alkylidene substituted by phenyl, cycloalkylidene of 5 to 7 ring carbon atoms, $SiR_2^4$ or $SnR_2^4$ where $R^4$ is $C_1$—$C_{12}$-alkyl, $C_5$-$C_{12}$-cycloalkyl, $C_6$-$C_{16}$-aryl or $C_7$-$C_{16}$-aralkyl; or said radical of formula Ii mono-substituted or polysubstituted by $C_1$—$C_{18}$-alkyl, by $C_1$—$C_{18}$-alkoxy, by $C_2$-$C_{18}$-alkenyl, by $C_5$-$C_8$-cycloalkyl, by $C_6$,$C_{16}$-aryl, by $C_7$—$C_{16}$-aralkyl, by cyano or by halogen;

$R^2$ is an 6-membered carbocyclic aromatic ring or a 5- or 6-membered heterocyclic aromatic ring which is substituted by fluorine atoms in at least one of the two ortho-positions relative to the metal-carbon bond, or $R^2$ and $R^3$ together are a radical of formula III
Q—Y—Q—(III)

in which Q is a carbocyclic aromatic ring, the two bonds in each case being in the ortho-position relative to the Y group, and the meta-position relative to the Y group in each case being substituted by a fluorine atom, or $R^2$ or Q is further substituted by alkyl or 1 to 18 carbon atoms, by alkoxy of 1 to 18 carbon atoms, by cycloalkyl of 5 to 6 ring carbon atoms, by aralkyl of 7 to 16 carbon atoms, by aryl of 6 to 16 carbon atoms, by hydroxyl, by carboxyl, by cyano, by halogen, by tertiary or quaternary amino, by alkoxycarbonyl of 1 to 18 carbon atoms in the alkoxy group, or by mono- or dialkylaminocarbonyl of 1 to 12 carbon atoms in the atoms alkyl group, Y is $CH_2$, alkylidene of 2 to 12 carbon atoms, cycloalkylidene of 5 to 7 ring carbon atoms, a direct bond, $NR^4$, O, S, SO, $SO_2$, CO, $SiR^4_2$ or $SnR^4_2$ where $R^4$ is defined above, $R^3$ has the same meaning as $R^2$, or $R^3$ is alkynyl of 2 to 6 carbon atoms, phenylethynyl or said phenylehtynyl substituted by halogen, by tertiary amino with 1 to 6 carbon atoms, by alkoxy of 1 to 6 carbon atoms, by carboxyl, by alkoxy or by cyano; $N_3$, CN, $SiR_3^4$ or $SnR_3^4$;

in which titanocenes $R^2$ contains at least one polyoxaalkylene radical of the formula $(—C_zH_{2z}O)_o—R^9$ in which z is a number from 2 to 6, o is a number from 1 to 20 and $R^9$ is H or $C_1$—$C_{18}$-alkyl, wherein said polyoxaalkylene radical is attached to the aromatic radical $R^2$ or Q by a direct bond or through a bridging group which is —S—, —O—, —$OSO_2$—, —CH—$_2$O—, —CH($CH_3$)—, —$SO_2$—, —C(O)O—

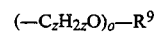

—$NR^{10}$—, $NR^{10}CH_2CH_2$—$NR^{10}$—$CH_2CH_2NR^{10}$—$CH_2NR^{10}$—, —CH-(COO—)$_2$, —$CH_2COO$—, —$CONR^{10}$—, —CH-($CONR^{10}$—)$_2$,

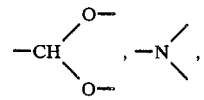

—OC(O)O—, —N($R^{10}$)—COO—, —$CH_2N(R^1$-$_0$)—COO—, —N($R^{10}$)—CONH—, —$CH_2N(R^1$-$_0$)—CONH— or —$C_nN_{2n}OC(O)C_mH_{2m}O$— where n=0, 1 or 2 and m=1-6, —$C_nH_{2n}OSiR_{3-y}^1$-$_{1}$O$_y$—, where and $R^{11}$ is $C_1$—$C_{12}$-alkyl or phenyl, where the valence on the left of the bridging group is attached to the aromatic ring R@ or Q and the other valences in the bridging group are attached to the polyoxaalkylene radical.

2. A titanocene according to claim 1, in which $R^1$ is cyclopentadienyl ⊖ or methylcyclopentadienyl⊖.

3. A titanocene according to claim 1, in which R² and R³ have the same meaning.

4. A titanocene according to claim 1, in which the alkylene is ethylene or 1,2-popylene.

5. A titanocene according to claim 1, in which R⁹ is $C_1$–$C_{18}$-alkyl, R¹⁰ is H or $C_1$–$C_{12}$-alkyl and R¹¹ is Cl–$C_6$-alkyl, is a number from 2 to 4 and o is a number from 2 to 6.

6. A titanocene according to claim 5, in which the polyoxaalkylene radical, together with the bridging group, corresponds to one of the formulae

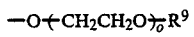

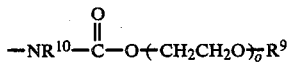

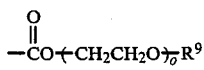

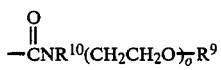

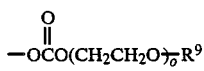

in which R⁹ is $C_1$–$C_{12}$-alkyl, R¹⁰ is H or $C_1$–$C_{16}$-alkyl and 0 is a number from 2 to 6.

7. A titanocene according to claim 1, of the formula I, in which R¹ is cyclopentadienyl⊖ or methycyclopentadienyl⊖ and R² and R³ are radicals of the formula

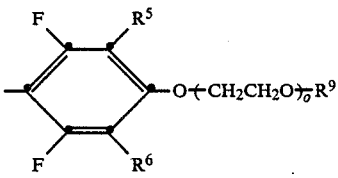

in which R⁵ and R⁶ are hydrogen or fluorine, o is a number from 2 to 6 and R⁹ is $C_1$–$C_{12}$-alkyl.

8. A titanocene according to claim 7, in which R⁵ and R⁶ are fluorine.

9. A titanocene according to claim 1 in which R² and R³ are 2,6-difluorophen-1-yl to which at least one polyoxalkylene radical where R⁹ is hydrogen or alkyl is bonded directly or through a bridging group, and which 2,6-difluorophen-I-yl group contains additionally one or two further identical or different substituents.

10. A titanocene according to claim 9 in which, in formula I, the two radicals R¹ are cyclopentadienyl⊖ or cyclopentadienyl⊖ which is substituted by $C_1$–$C_4$-alkyl, and R² and R³ are radicals of the formula

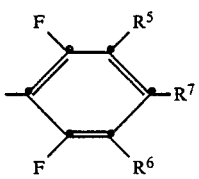

in which R⁵ and R⁶ independently of one another are H, F, Cl or Br, and R⁷ is a polyoxaakylene radical which is bonded to the phenyl ring directly or through a bridging group.

11. A titanocene according to claim 1 where in the polyoxaalkylene radical R⁹ is $C_1$–$C_{18}$-alkyl.

12. A titanocene according to claim 1 which is bis(cyclopentadienyl)-bis-[4-(1,4,7-trioxa-n-undec-1-yl)-2,3,5,6-tetrafluorophenl]titanocene.

* * * * *